United States Patent
Klemm et al.

(10) Patent No.: US 11,813,437 B2
(45) Date of Patent: *Nov. 14, 2023

(54) SENSOR DEVICE FOR A DRUG DELIVERY DEVICE

(71) Applicant: Sanofi-Aventis Deutschland GMBH, Frankfurt am Main (DE)

(72) Inventors: Thomas Klemm, Frankfurt am Main (DE); Dmitri Bogatirsky, Frankfurt am Main (DE); Mihaly Gabli, Frankfurt am Main (DE); Stefan Bohling, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 335 days.

This patent is subject to a terminal disclaimer.

(21) Appl. No.: 17/181,588

(22) Filed: Feb. 22, 2021

(65) Prior Publication Data

US 2021/0178075 A1 Jun. 17, 2021

Related U.S. Application Data

(63) Continuation of application No. 15/748,042, filed as application No. PCT/EP2016/067344 on Jul. 20, 2016, now Pat. No. 10,926,034.

(30) Foreign Application Priority Data

Jul. 29, 2015 (EP) ..................................... 15178750

(51) Int. Cl.
*G01C 3/08* (2006.01)
*A61M 5/24* (2006.01)
(Continued)

(52) U.S. Cl.
CPC .......... *A61M 5/24* (2013.01); *A61M 5/31553* (2013.01); *G01D 5/202* (2013.01);
(Continued)

(58) Field of Classification Search
None
See application file for complete search history.

(56) References Cited

U.S. PATENT DOCUMENTS

| 5,704,922 A | 1/1998 | Brown |
| 6,964,862 B2 | 11/2005 | Chen |

(Continued)

FOREIGN PATENT DOCUMENTS

| CN | 1671432 | 9/2005 |
| CN | 101268336 | 9/2008 |

(Continued)

OTHER PUBLICATIONS

PCT International Preliminary Report on Patentability in International Appln. No. PCT/EP2016/067344, dated Jan. 30, 2018, 7 pages.

(Continued)

*Primary Examiner* — Mark Hellner
(74) *Attorney, Agent, or Firm* — Fish & Richardson P.C.

(57) ABSTRACT

A sensor device to be attached to a drug delivery device includes an array of conducting elements each forming part of a respective resonant circuit and each operable to have a signal applied to it. The drug delivery device has a first movable element supporting a conductive region, which is configured to move along a path parallel to a longitudinal axis of the drug delivery device. When the sensor device is attached to the drug delivery device, the conducting elements are arranged such that each resonant circuit is operable to output a signal indicative of the proximity of the conductive region supported on the first moveable element (Continued)

to the respective conducting element of each resonant circuit. The sensor device includes circuitry to receive the signals output from the resonant circuit and, based on the received signals, determines information associated with a location along the path of the first movable element.

20 Claims, 11 Drawing Sheets

(51) Int. Cl.
    *G01D 5/20* (2006.01)
    *A61M 5/315* (2006.01)
    *A61M 5/00* (2006.01)

(52) U.S. Cl.
    CPC ....... *A61M 5/002* (2013.01); *A61M 2205/502* (2013.01); *A61M 2205/52* (2013.01)

(56) References Cited

U.S. PATENT DOCUMENTS

| | | | |
|---|---|---|---|
| 9,517,303 | B2 | 12/2016 | Bazargan et al. |
| 2006/0290346 | A1 | 12/2006 | Habenschaden et al. |
| 2016/0131572 | A1 | 5/2016 | Klein |
| 2017/0072140 | A1* | 3/2017 | Bazargan .......... A61M 5/16831 |

FOREIGN PATENT DOCUMENTS

| | | |
|---|---|---|
| CN | 103717247 | 4/2014 |
| CN | 103957961 | 7/2014 |
| CN | 104519931 | 4/2015 |
| EP | 1672323 | 6/2006 |
| JP | 2008-267922 | 11/2008 |
| JP | 2014-520616 | 8/2014 |
| JP | 2014-531283 | 11/2014 |
| JP | 2015-506771 | 3/2015 |
| JP | 2015-528318 | 9/2015 |
| JP | 2016-512966 | 5/2016 |
| JP | 2016-515451 | 5/2016 |
| JP | 2016-534370 | 11/2016 |
| JP | 2018-507068 | 3/2018 |
| WO | WO 2004/009163 | 1/2004 |
| WO | WO 2007/039148 | 4/2007 |
| WO | WO 2008/145171 | 12/2008 |
| WO | WO 2011/117212 | 9/2011 |
| WO | WO 2013/010889 | 1/2013 |
| WO | WO 2013/050535 | 4/2013 |
| WO | WO 2013050535 | * 4/2013 .......... A61M 5/1452 |
| WO | WO 2013/110538 | 8/2013 |
| WO | WO 2013/120778 | 8/2013 |
| WO | WO 2014/023763 | 2/2014 |
| WO | WO 2014/111341 | 7/2014 |
| WO | WO 2014/111342 | 7/2014 |
| WO | WO 2014/173770 | 10/2014 |
| WO | WO 2015/039134 | 3/2015 |
| WO | WO 2016/142216 | 9/2016 |

OTHER PUBLICATIONS

PCT International Search Report and Written Opinion in International Appln. No. PCT/EP2016/067344, dated Oct. 24, 2016, 10 pages.

* cited by examiner

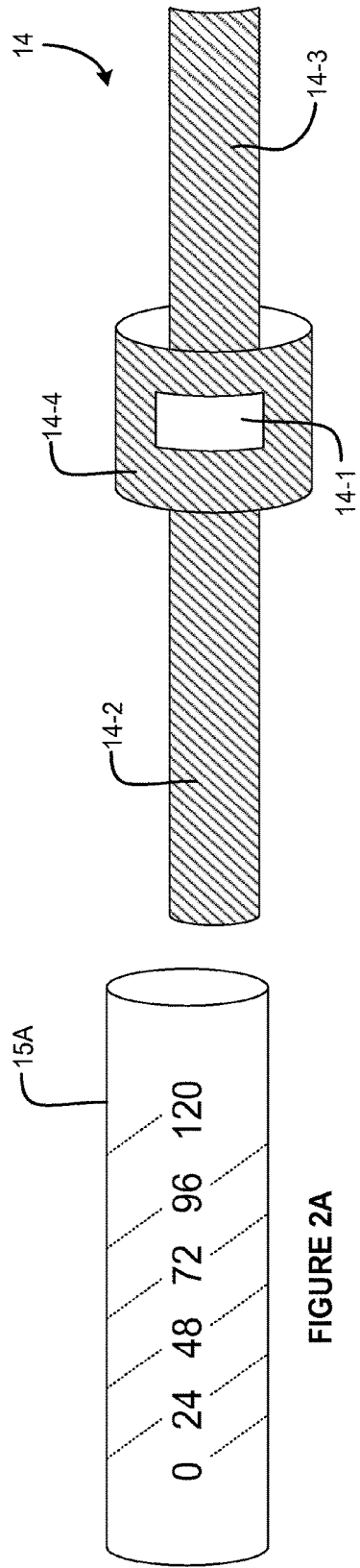
FIGURE 2A
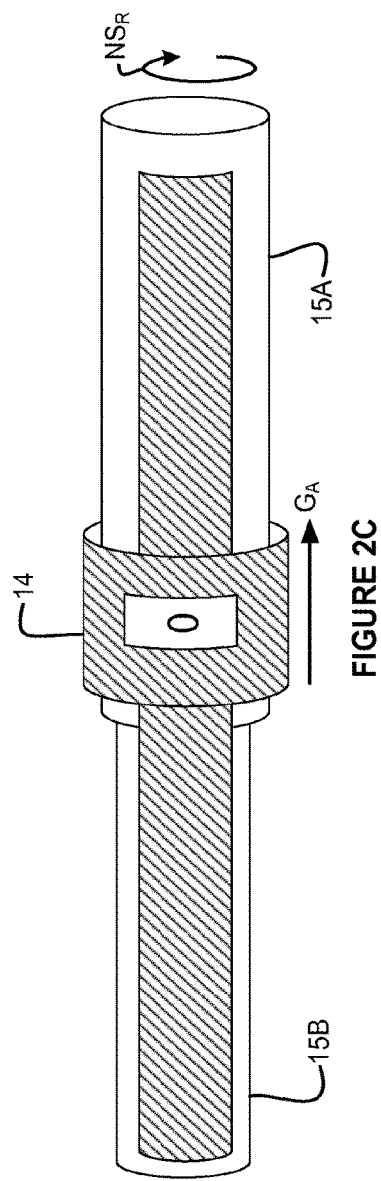
FIGURE 2B
FIGURE 2C
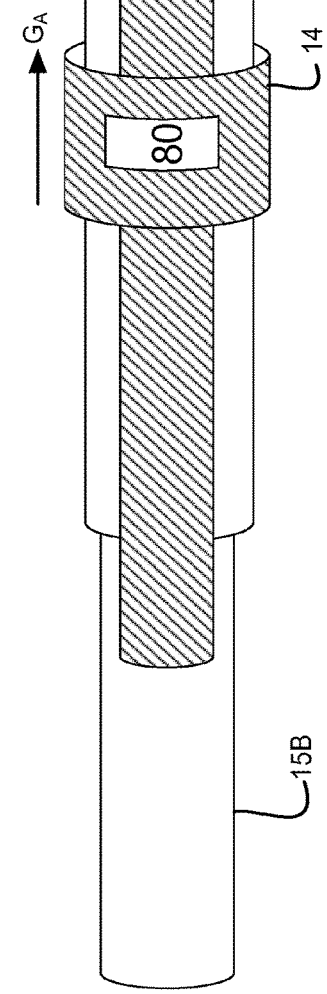
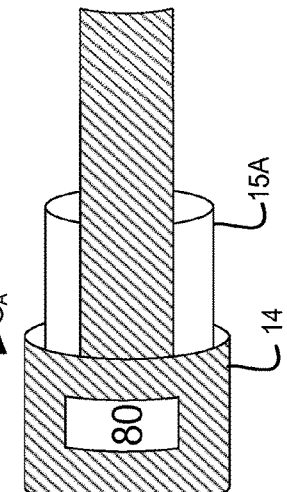
FIGURE 2D

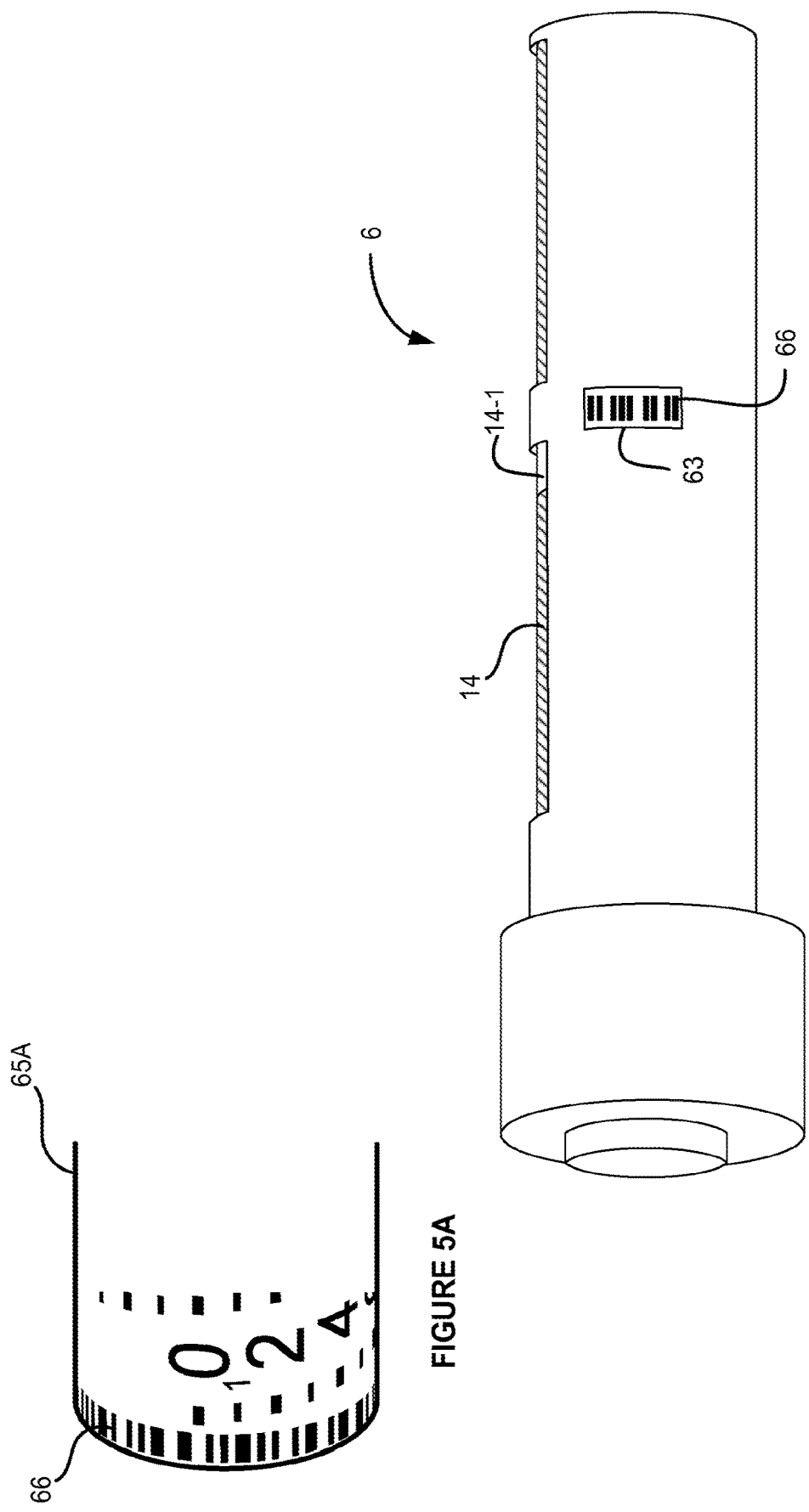

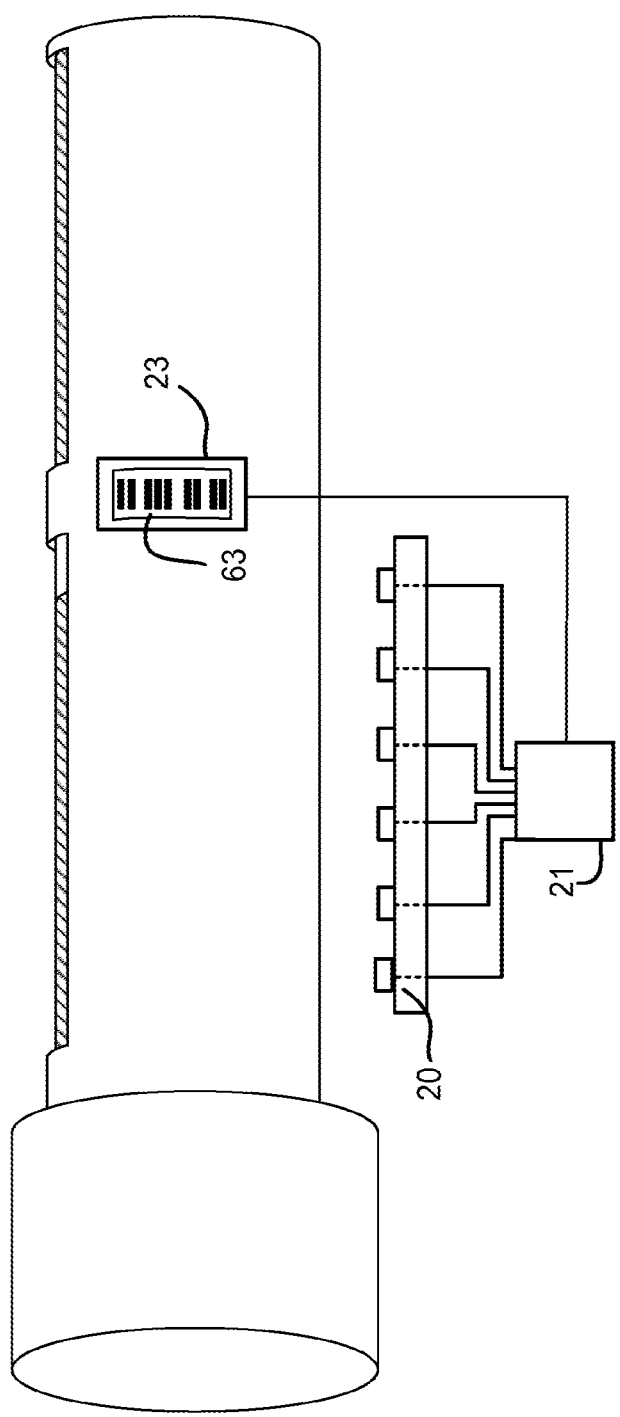

SENSOR DEVICE FOR A DRUG DELIVERY DEVICE

CROSS REFERENCE TO RELATED APPLICATIONS

The present application is a continuation of U.S. patent application Ser. No. 15/748,042, filed Jan. 26, 2018, which is the national stage entry of International Patent Application No. PCT/EP2016/067344, filed on Jul. 20, 2016, and claims priority to Application No. EP 15178750.4, filed in on Jul. 29, 2015, the disclosures of which are expressly incorporated herein in entirety by reference thereto.

TECHNICAL FIELD

The disclosure relates to a sensor device which is removably attachable to a drug delivery device such as an injection pen.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning (dialing) a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin type and dose.

It has been described, for instance in WO 2011/117212, to provide a supplementary device comprising a mating unit for releasably attaching the device to an injection/drug delivery device. The device includes a camera and is configured to perform optical character recognition (OCR) on captured images visible through a dosage window of the injection pen, thereby to determine a dose of medicament that has been dialed into the injection device. In order for such a supplementary device to successfully determine the dose, the dosage window must remain stationary. However not all drug delivery devices operate in this way.

SUMMARY

A first aspect of the disclosure provides a sensor device configured to be removably attached to a drug delivery device, the sensor device comprising:
an array of conducting elements each forming part of a respective resonant circuit and each operable to have a signal applied to it, wherein the array of conducting elements are arranged within the sensor device such that, when the sensor device is attached to the drug delivery device, the drug delivery device having a first movable element which is configured to move along a path parallel to a longitudinal axis of the drug delivery device and which supports thereon a conductive region, each resonant circuit is operable to output a signal indicative of the proximity of the conductive region supported on the first moveable element to the respective conducting element of each resonant circuit; and
circuitry configured to receive the signals output from the resonant circuit and, based on the received signals, to determine information associated with a location along the path of the first movable element.

Each of the resonant circuits may have a different resonance frequency.

The array of conducting elements may be arranged within the sensor device such that, when the sensor device is attached to the drug delivery device, the conducting elements of the array are generally equidistantly spaced from one another along a length corresponding to the maximum extend of movement of the moveable element.

Each conductive element in the array may comprise at least one metal coil.

The circuitry may be configured to measure the amplitude of the resonant signal output from each of the resonant circuits and to determine an amount of damping of each resonant signal due to the proximity of the conductive region supported on the first moveable element.

The sensor device may further comprise a sensing arrangement arranged within the sensor device such that, when the sensor device is attached to the drug delivery device, the sensing arrangement is operable to read encoded information that is externally visible on the drug delivery device, wherein the circuitry is configured to determine, based on the encoded information, information relating to operation of the drug delivery device.

The circuitry may be configured to determine based on the encoded information and the location along the path of the first movable element, information relating to a drug dose to which the drug delivery device is currently dialed.

At least part of the encoded information may be provided on at least a second movable element of the drug delivery device, the second movable element being rotatable within the drug delivery device and the circuitry may be configured to determine based on the encoded information a degree of rotation of the second movable element within the drug delivery device.

The circuitry may be configured to determine the information relating to the currently-dialed drug dose based on the location along the path of the first movable element and the degree of rotation of the second movable element.

The circuitry may be configured to determine a dose size to be dispensed and/or a dose size dispensed based on the information relating to the currently-dialed drug dose.

The circuitry may be configured to determine based on the encoded information an operational mode of the drug delivery device.

The circuitry may be configured to determine a change from a dialing mode to a dispense mode. The circuitry may alternatively or additionally be configured to determine a change from a dispense mode to a dialing mode.

The determination of a change in operational mode may be used to further process information relating to the currently-dialed dose.

At least part of the encoded information may be externally visible through an aperture or window formed in the delivery device, wherein the sensing arrangement may be arranged within the sensor device such that, when the sensor device is attached to the drug delivery device, the sensing arrangement is operable to detect light received from the aperture or window.

The sensing arrangement may comprise a light source arrangement configured to project light towards the aperture or window in the drug delivery device when the sensor device is attached to the drug delivery device and a photosensor arrangement configured to receive light reflected from the aperture or window.

The sensor device may be configured to store a history of dispensed drug doses. This may be carried out by storing information indicative of the currently dialed dose. For example, when a change in an operational mode of the drug delivery device is detected the currently dialed dose information can indicate a dose that is to be dispensed. The sensor device may store this as a dispensed drug dose. Alternatively or additionally, the sensor device may be configured to determine the dispensed drug dose. For example, the dispensed dose may be calculated from the currently dialed dose and the zero dose that is determined at the end of the dispense action. Alternatively, the dispensed dose may be calculated from the currently dialed dose at time the sensor device determines a change in operational mode from dialing mode to dispense mode and a currently dialed dose at a time the sensor device determines a change in operational mode from dispense mode to dialing mode.

A timestamp indicative of a time at which the change in an operational mode occurred may also be stored in association with the information indicative of the dose.

In addition or alternatively, information indicative of the type of the dispensed drug or medicament may be stored in association with the dose information.

Storing at least one of information relating to a dispensed dose, a timestamp, and information indicative of the type of dispensed drug or medicament may be repeated each time a dose of a drug is dispensed.

The sensor device may therefore be configured to store a history of dispensed drug doses based on at least information relating to an operation mode of the drug delivery device and information relating to a drug dose to which the drug delivery device is currently dialed.

The type of drug or medicament may be determined based on a drug indication code. The drug indication code may be arranged on an outside of a drug delivery device. The drug indication code may be arranged such that it is visible from an outside of a drug delivery device. The sensor device may comprise a sensor configured to detect the drug indication code.

A second aspect of the disclosure provides a drug delivery system comprising the sensor device of the first aspect of the disclosure and a drug delivery device having the first movable element which is configured to move along the path.

The first movable element may be moveable along an underlying element and may be configured such that movement of the first movable element in a particular direction causes the underlying element to become externally visible at successive locations along the path.

The drug delivery device may comprise a second movable element which is rotatable within the device, wherein rotation of the second movable element and movement of the first movable element are interdependent. The second movable element may comprise a code provided around a portion of its exterior, a part of the code being externally visible through a window or aperture formed in the drug delivery device.

The sensor device may comprise a sensing arrangement overlying the window or aperture and configured to read the portion of the code that is externally visible through the window or aperture. The circuitry may be configured to determine, based on the externally visible portion of the code and the position along the path of the first movable element, information relating to drug dose to which the drug delivery device is currently dialed.

BRIEF DESCRIPTION OF THE FIGURES

For a more complete understanding of example embodiments of the present invention, reference is now made to the following description taken in connection with the following Figures, in which:

FIGS. 2A to 2E are illustrative simplified views of various components, and combinations of components, of a drug delivery device such as that of FIG. 1 with which a sensor device according to various embodiments may be used;

FIGS. 5A and 5B are illustrative simplified views of various components of an alternative drug delivery device with which sensor devices according to various embodiments of the disclosure may be used;

FIG. 5C is a simplified view of a sensor device according to embodiments of the disclosure in combination with the drug delivery device of FIGS. 5A and 5B;

DETAILED DESCRIPTION

Figure 1:
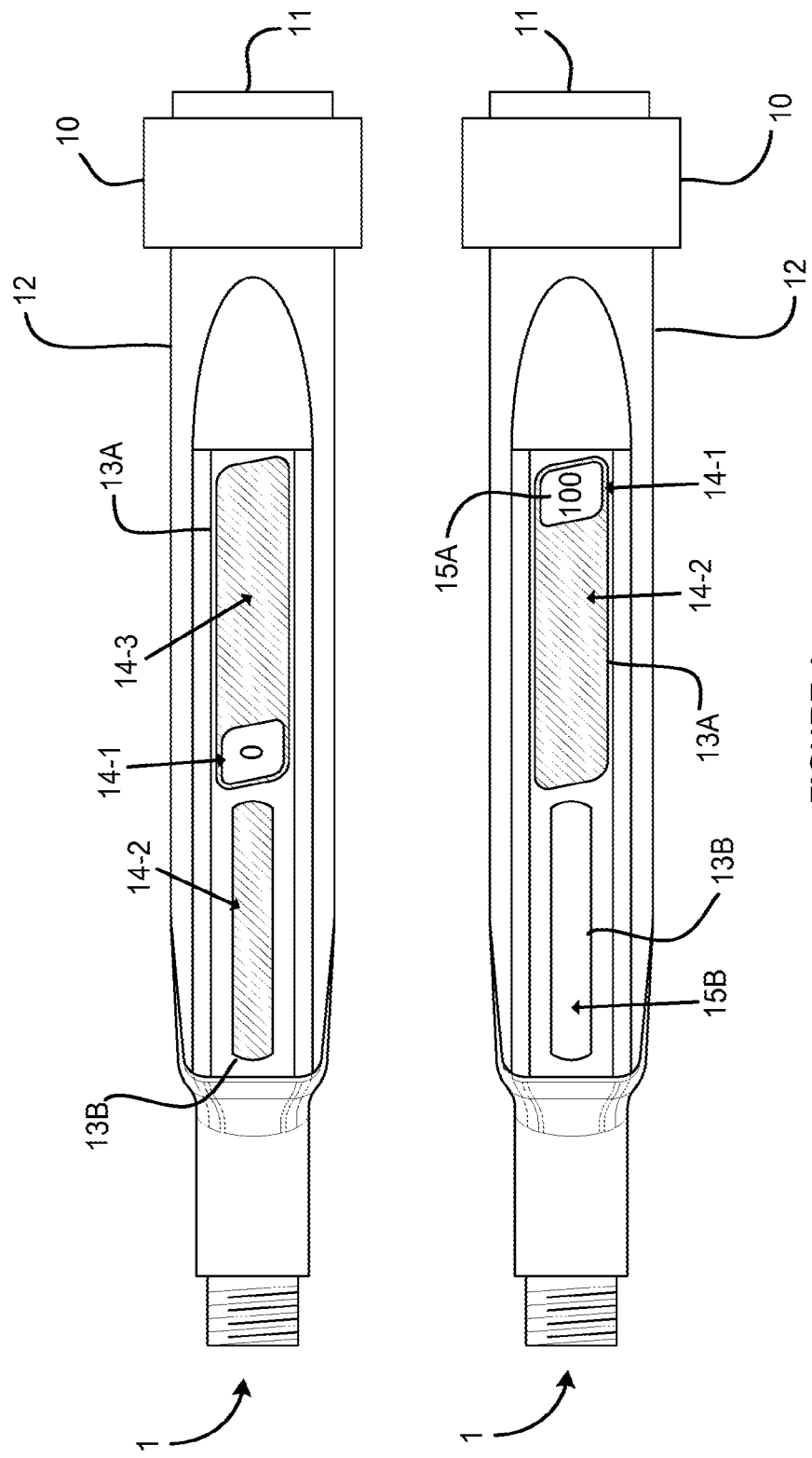
FIG. 1 shows two views of a drug delivery device 1 with which a sensor device according to various embodiments of the disclosure may be used.

In the description and drawings, like reference numerals refer to like elements throughout. FIG. 1 shows two views of a drug delivery device 1, in this example an injection device, with which a sensor device (also referred to as a supplementary device—not shown) according to various embodiments of the invention may be used.

The drug delivery device 1 of FIG. 1 is configured such that a user is able to adjust the drug dosage (or number of drug doses) that is to be delivered (or dispensed or ejected) using the device 1. In the example of FIG. 1, this is achieved by rotating (or dialing) a dose selector 10 which causes an internal dialing mechanism (not shown) to adjust an amount of the drug that is to be dispensed once a drug delivery mechanism (not shown) is actuated. In this example, the drug delivery mechanism is actuated by pressing a button 11 on the device.

The drug delivery device 1 comprises an external housing 12 in which is formed at least one aperture or window 13A, 13B. As will be appreciated, an aperture may simply be a cut-away area of the external housing 12, whereas a window may be a transparent portion of the housing through which components of the device may be seen. For convenience, the at least one aperture or window 13A, 13B, will hereafter simply be referred to as the at least one window.

The at least one window 13A, 13B allows a movable gauge element 14 to be visible from the exterior of the housing 12. The drug delivery device is configured such that as the dose selector 10 is dialed, the movable gauge element 14 is caused to be moved thereby to indicate a selected dose to the user. More specifically, as the dose selector 10 is dialed, the gauge element 14 moves axially along an underlying surface 15A, 15B thereby to indicate the selected dose. In the example of FIG. 1, a surface 15A underlying at least part of the gauge element 14 comprises a number sleeve 15A. The number sleeve 15A has numbers indicative of drug doses provided on its outer surface, with the number indicating the currently selected dose being visible through the at least one window 13A, 13B. In this example, the number sleeve 15A is visible through a gauge window (or aperture) 14-1 formed in the movable gauge element. Other parts of the movable gauge element 14 are discussed below.

The uppermost view of the drug delivery device 1 shown in FIG. 1 illustrates the situation before any dialing has been performed. Consequently, the movable gauge element 14 is at its first (or initial) position at a first end of the path along which it is able to move. In this example, when the movable gauge element 14 is at the first end of its path, the portion of the number sleeve 15A that is visible through the gauge window 14-1 shows the number zero (i.e. a zero dose). The same number zero is also shown at the end of a dispense action, when a user has pressed button 11 of drug delivery device 1 to completely dispense or deliver the adjusted dose.

The bottommost view of the drug delivery device 1 shown in FIG. 1 illustrates the situation after dialing has been performed. Consequently, the movable gauge element 14 has moved axially along the path that is visible through the first window 13A away from its first position. In this example, the device 1 has been dialed to its maximum dose and as such, the movable gauge element 14 has moved to the second end of its path. The maximum dose in this example is "100" and so the portion of the number sleeve 15A that is visible through the gauge window 14-1 shows the number "100". In some other embodiments, the maximum dose may be larger or smaller than this. For example, in some embodiments, the maximum dose may be "120".

In this example, the device 1 comprises first and second windows 13A, 13B. The number sleeve 15A underlies and is visible through the first window 13A, whereas a further underlying element 15B underlies and is sometimes visible through the second window 13B. The further underlying element 15B may or may not include any numbers. The further underlying surface 15B is visually distinguishable from a second part 14-2 of the movable gauge element 14 which overlies it and which is configured to move axially along it. For instance, the second part 14-2 of the movable gauge element 14 may be of a different colour, hue or reflectance to the further underlying surface 15B. For example, one of the gauge element 14 and the underlying surface 15B may be of a light colour (e.g. may be made of a light coloured polymer) and the other may be of dark colour (e.g. may be made of a dark coloured polymer). The user may, therefore, be able to determine the selected dose by determining the proportion of the second window 13A in which the gauge element 14 (specifically, the second part 14-2) is visible compared to the proportion in which the further underlying surface 15B is visible. This can be seen from FIG. 1, in which, when the device 1 is dialed to its zero dose, the gauge element 14 covers the entire length of the path that is visible through the second window 13B. In contrast, when the device 1 is dialed to its maximum dose, none of the gauge element 14 is visible through the second window. Instead, the further underlying surface 15B is visible along the entire length of the path defined by the second window 13B.

The number sleeve 15A (which is also the surface underlying the gauge element 14) is also visually distinguishable from the movable gauge element 14 which overlies it and which is configured to move axially along it. For instance, gauge element 14 may be of a different color, hue or reflectance to the number sleeve 15A. For example, one of the gauge element 14 and the underlying surface 15A may be of a light color (e.g. may be made of a light colored polymer) and the other may be of dark color (e.g. may be made of a dark colored polymer). In the examples shown in the Figures, the number sleeve 15A and underlying surface 15B are of a higher reflectance than the movable gauge element 14.

FIGS. 2A to 2E are simplified schematics of components of a drug delivery device such as that of FIG. 1. The purpose of FIGS. 2A to 2E is to illustrate the operation of a drug delivery device 1 such as that of FIG. 1; they are not intended to be accurate representations of the exact design of the components.

FIG. 2A is a simplified schematic of the number sleeve 15A. The sleeve 15A has numbers provided on its surface. In some examples, the numbers, ranging from the minimum dose to the maximum dose, may be provided helically around the surface of the number sleeve. Due to space restrictions and the need for the numbers to be legible, not every number may be printed on the number sleeve 15A. For example, only even numbers may be printed.

FIG. 2B is a simplified schematic of a movable gauge element 14. The gauge element 14 comprises a first section 14-4 in which the gauge window 14-1 is provided. In this example, the first section is 14-1 a collar which is configured to encircle the number sleeve 15A (as can be seen in FIGS. 2C and 2D). Extending in opposite directions from the first section 14-4 are the second part 14-2 and a third part 14-2. The second and third parts 14-2, 14-3 extend generally parallel to the longitudinal axis of the number sleeve.

The second part 14-2 of the movable gauge element is configured to extend from the first part 14-2 by a length sufficient to fill the entire second window 13B when the movable gauge is in its first position. The second part 14-2 may also serve to obscure a portion of the exterior surface of the number sleeve 15A, when the gauge element moves away from its first position. The third part of the movable gauge element 14-3 is configured to obscure a portion of the exterior surface of the number sleeve 15A, when the gauge element moves between its first and second positions. In this way, only the portion of the number sleeve that underlies the gauge window 14-1 is visible through the first window 13A of the device housing 12. In the example depicted, the second and third parts 14-2, 14-3 do not fully encircle the number sleeve 15A and are wide enough only to cover the first window 13A. However, in some other embodiments, the second and third parts 14-2, 14-3 may partially or entirely encircle the underlying elements 15A, 15B.

The number sleeve 15A is rotatable about its longitudinal axis within the device housing 12. As such, the number sleeve 15A may be referred to as a movable (or rotatable) element. Rotation of the number sleeve 15A is in some embodiments caused by rotation of the dose selector 10.

The rotational movement $NS_R$ of the number sleeve 15A and axial movement $G_E$ of the gauge element 14 are interdependent. Put another way, the dialing mechanism of the device 1 is configured such that when number sleeve 15A is caused to rotate, the gauge element 14 is caused to move or translate axially along its path. Moreover, the degree of rotation of the number sleeve 15A corresponds proportionally to the extent of axial movement of the gauge element 14.

Figure 2E:
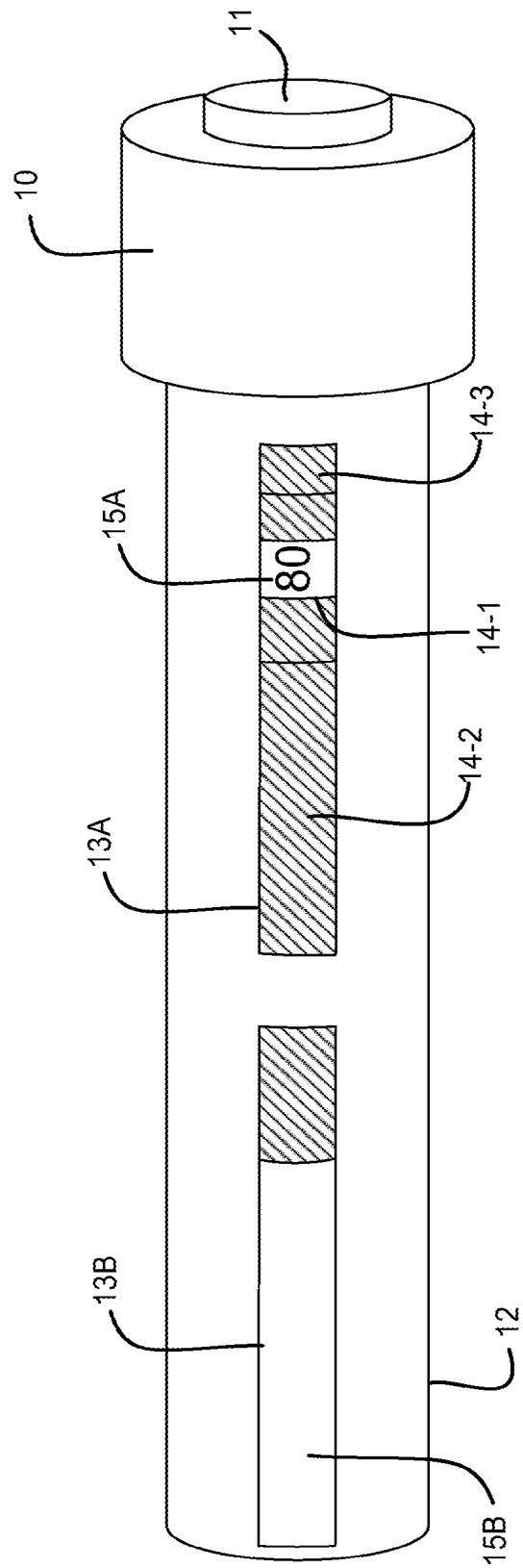

FIG. 2C shows the gauge element 14 in its initial position in which, in this example, it indicates a zero dose. FIG. 2D shows the number sleeve 15A and gauge element 14 following rotation of the number sleeve 15A and translation of the gauge element 14 from its first position. FIG. 2E shows this arrangement of FIG. 2D within a simplified version of the device housing 12.

Various dialing mechanisms for adjusting a dose to be delivered to a user which transform rotation of a dose selector 10 into rotational movement of a number sleeve 15A and axial movement of a gauge element 14 (as described above) are known in the art. Two such mechanisms are described in WO2013/110538A1 and WO2008/145171A1. As such mechanisms (and also drug delivery mechanisms which cause delivery of the drug once the dose has been dialed) are known in the art, they will not be described herein in any detail.

Figure 3:
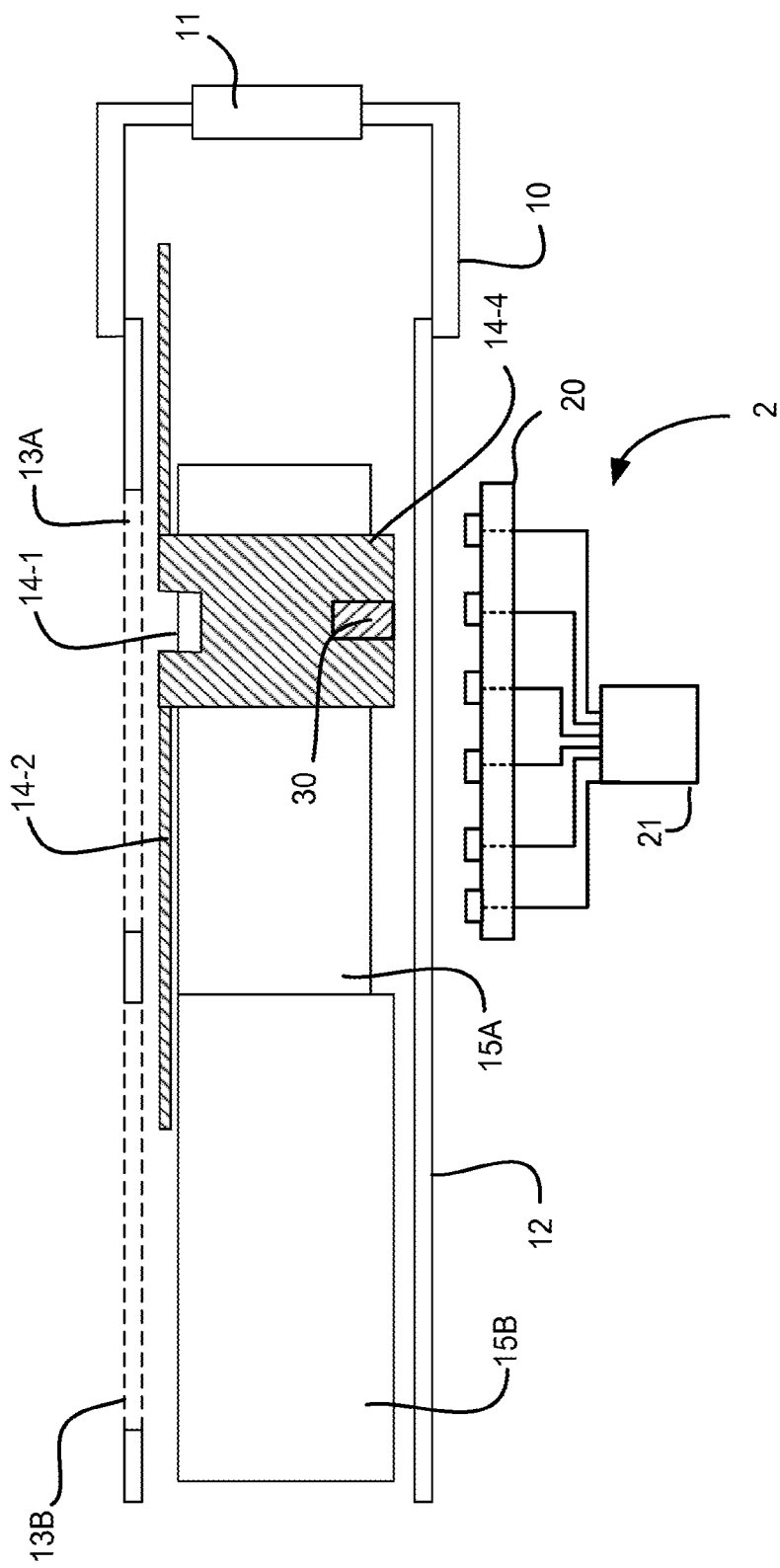
FIG. 3 shows is a simplified cut-away view of the drug delivery device components depicted in FIG. 2D in combination with part of a sensor device according to various embodiments of the disclosure.

FIG. 3 shows an extremely simplified cut-away view of the components of the delivery device 1 as depicted in FIG. 2D and a simplified schematic illustration of a sensor device 2 for use with a delivery device 1 such as that described with reference to FIGS. 1 to 2D.

The sensor device 2 comprises an array 20 of conducting elements 20-1 to 20-6. The sensor device 2 further comprises circuitry 21. Each conducting element is configured to have an alternating current of a predetermined frequency applied to it by one or more oscillators (or a circuit equivalent) forming part of the circuitry 21. In some embodiments, each of the conducting elements 20-1 to 20-6 is a metal coil. The coils may be easily printed onto a PCB and may be generally identical. In other embodiments, different arrangements and shapes of conducting element may be used. For example, the coils may be different in size and/or have different number of windings. The coils may be two dimensional or three dimensional. Stacking coils in a three dimensional way increases the EM field generated when a signal is applied to them. In some embodiments, the PCB supports six conducting elements 20-1 to 20-6. The amplitude of the resonance of each resonant circuit is dominated by its coil. In some embodiments, it is therefore desirable that each coil is identical in size and construction.

The conducting elements/coils 20-1 to 20-6 are arranged within the sensor device 2 such that they are close to the part of the housing of the sensor device 2 which is adjacent the drug delivery device 1 when the two are connected together. When the sensor device 2 is in place adjacent the drug delivery device 1, the conducting elements 20-1 to 20-6 of the array 20 are spaced along a path over which the gauge element 14 travels. The conducting elements 20-1 to 20-6 may be substantially equidistantly spaced from one another along a length generally corresponding to the maximum extent of movement of the gauge element 14. The axis along which the array 20 extends is generally parallel to the longitudinal axis of the drug delivery device 1. The length over which the gauge element 14 travels (which is approximately equal to the size of the first window 13A) is, in one design, 3 cm. This means that the coils can be comfortably accommodated on a PCB with a separation of 5-6 mm.

As can also be seen in FIG. 3, the gauge element 14 comprises a conductive region 30. In the embodiment depicted, the conductive region 30 is disposed on the rear of the first section 14-4 of the gauge element 14, i.e. on the side opposite the gauge window 14-1. The conductive region 30 on the gauge element 14 may be a conductive ink or varnish, a metal foil or a metal plate or inlay. The conductive region 30 may be composed of aluminum or copper, for example. In another example, the conductive region 30 may be composed of ferro-magnetic material, such as iron, nickel, cobalt, and most of their alloys, or other ferro-magnetic materials known in the art. In some embodiments, the conductive region 30 may have a width of 5 mm.

The sensor device 2 is configured to be mounted on the drug delivery device 1 such that the conducting elements 20-1 to 20-6 within the sensor device 2 lie adjacent to the conductive region 30 within the drug delivery device 1. Therefore, the sensor device 2 is configured to be mounted such that at least a part of it extends to the rear of the drug delivery device 1. This may be advantageous, as the sensor device 2 does not then obscure the gauge window 14-1 or the first and second windows 13A, 13B or interfere with the dialing and dispensing of a medicament dose. In some designs, the second and third parts 14-2, 14-3 partially or fully encircle the number sleeve 15A and the conductive region 30 may alternatively be disposed on one of these parts. The skilled person will appreciate that the conductive region 30 on the gauge element 14 may be offset relative to the gauge window 14-1 by some other amount, for example by 90 degrees.

In some embodiments an oscillator, forming part of the circuitry 21, is used to apply a resonating signal to each of the conducting elements/coils simultaneously. The circuitry may comprise one or more band pass filters to improve the quality of the applied signals. Each of the conducting elements 20-1 to 20-6 has an associated capacitor, where the oscillator, capacitor and conducting element/coil together form a resonant circuit. The skilled person will be aware that other circuit components, such as resistors, may be required to construct a functioning resonant circuit. Each resonant circuit formed by the oscillator, capacitor, conducting element, and optionally resistor has a specific resonant frequency. The resonant frequency of each of the resonant circuits may be slightly different. For example, each capacitor may have a different capacitance such that the resonant frequency of each of the resonant circuits is slightly different. Alternatively or additionally, each coil may have different inductance, such that the resonant frequency of each of the resonant circuits is slightly different. Further alternatively or additionally, each or some resonant circuit(s) may have a different resistance, such that the resonant frequency of each of the resonant circuits is slightly different. This helps to avoid unwanted interaction between the magnetic fields generated by each coil 20-1 to 20-6. This also helps in identifying the output signals of each resonant circuit. In some embodiments, only adjacent resonant circuits may have different resonating frequencies. For example, resonant circuits 1, 3 and 5 may have a first frequency while resonant circuits 2, 4 and 6 may have a second resonant frequency. Ideally, there should be no, or very little, overlap between the bandwidth of each of the resonant circuits so that the signals from each circuit can be readily distinguished. In some embodiments, the resonant circuits each have a relatively high Quality factor (Q factor) such that the frequencies of adjacent resonant circuits can be similar without overlapping. As the amplitude of the resonance of each resonant circuit is dominated by the coil, it is desirable in some embodiments that the coils are identical and that the differences in resonant frequency of the resonant circuits are achieved by using capacitors of differing capacitance.

The circuitry 21 of the sensor device 2 is configured to receive signals output from the conducting elements 20-1 to 20-6 of the array 20 and, based on the received signals, to determine information associated with a location of the gauge element 14. The proximity of the conductive region 30 of the gauge element 14 to one of the conducting elements 20-1 to 20-6, causes a reduction in the quality of the resonance in that element. The proximity of another conductive region has a damping effect (due to Eddy current losses) and causes the amplitude of the resonant signal to be decreased. Thus it is possible to determine which one of the array of conducting elements 20-1 to 20-5 is closest to the conductive region 30, as will be explained below in greater detail.

FIGS. 4A to 4E illustrate the operation of the sensor device 2 when the movable element is at different positions along its path. In this example, the array 20 comprises first to sixth conducting elements 20-1 to 20-6, with the first element 20-1 being located adjacent the conductive region 30 of the movable gauge element 14 when the minimum dose is dialed. The sixth sensor 20-6 is located adjacent the conductive region 30 of the movable gauge element 14 when the maximum dose is dialed.

Figure 4A:
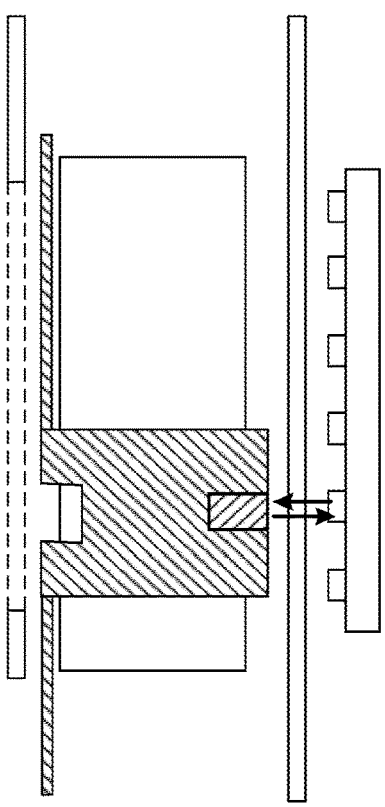
FIGS. 4A to 4D show various views of the drug delivery device and the sensor array of the sensor device of FIG. 3 for the purpose of illustrating the operation of the sensor device.

In FIG. 4A, the movable gauge element 14 is at its initial position (e.g. when the dose is at its minimum). Consequently, the quality of the resonance in the first conducting element 20-1 is lower than in all of the other conducting elements. In some embodiments, the proximity of the conductive region 30 may reduce the amplitude of the resonance in the first conducting element 20-1 to near zero.

Figure 4B:
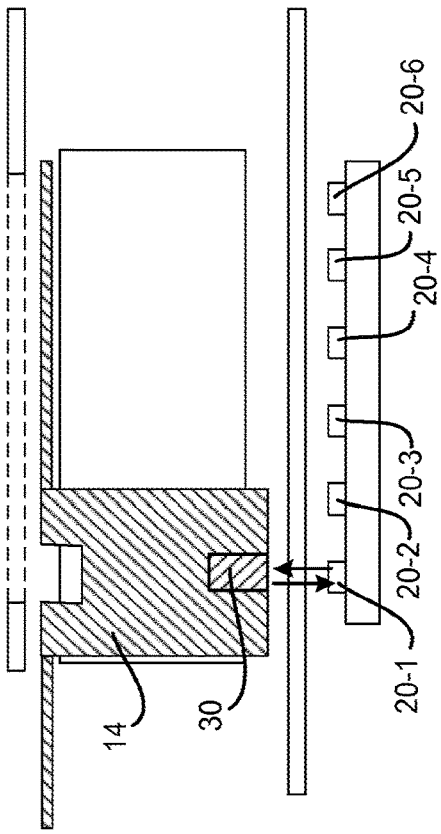

In FIG. 4B, the gauge element 14 has moved to approximately the 20% dose position. In this situation, the quality of the resonance in the second conducting element 20-2 is lower than in all of the other conducting elements. It can be appreciated from FIG. 2A that this position corresponds to approximately one complete rotation of the number sleeve 15A.

Figure 4C:
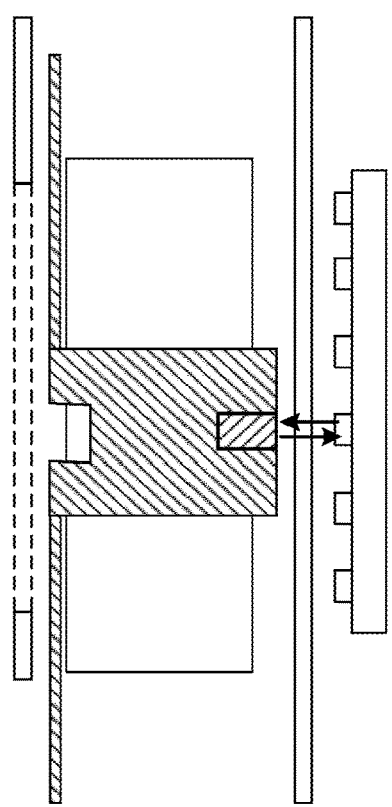

In FIG. 4C, the gauge element 14 has moved to approximately the 40% dose position and so the third conduction element 20-3 has a low quality of resonance, while the first, second, fourth, fifth and sixth elements have a high quality resonance. It can be appreciated from FIG. 2A that this position corresponds to approximately two complete rotation of the number sleeve 15A.

Figure 4D:
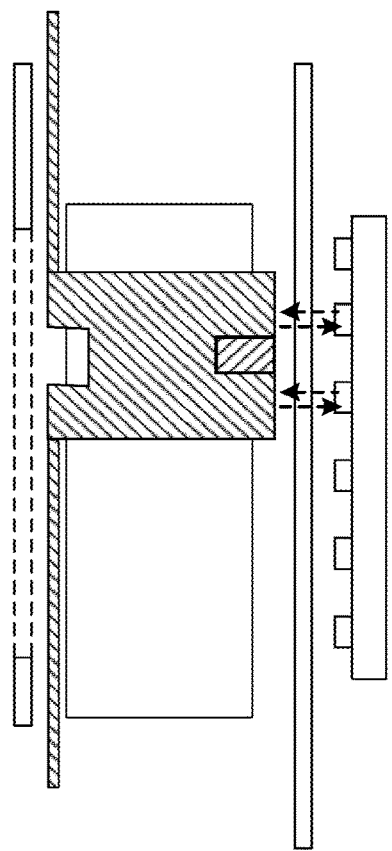

Finally, in FIG. 4D, the gauge element 14 has moved to approximately the 70% dose position. In this position, the conductive region 30 is located between the fourth and fifth elements such that both the fourth element 20-4 and the fifth element 20-5 have the quality of their resonance reduced due to the proximity of the conductive region 30. However, the reduction in quality is less than when the conductive region 30 is located directly beneath a conductive element.

Figure 4E:
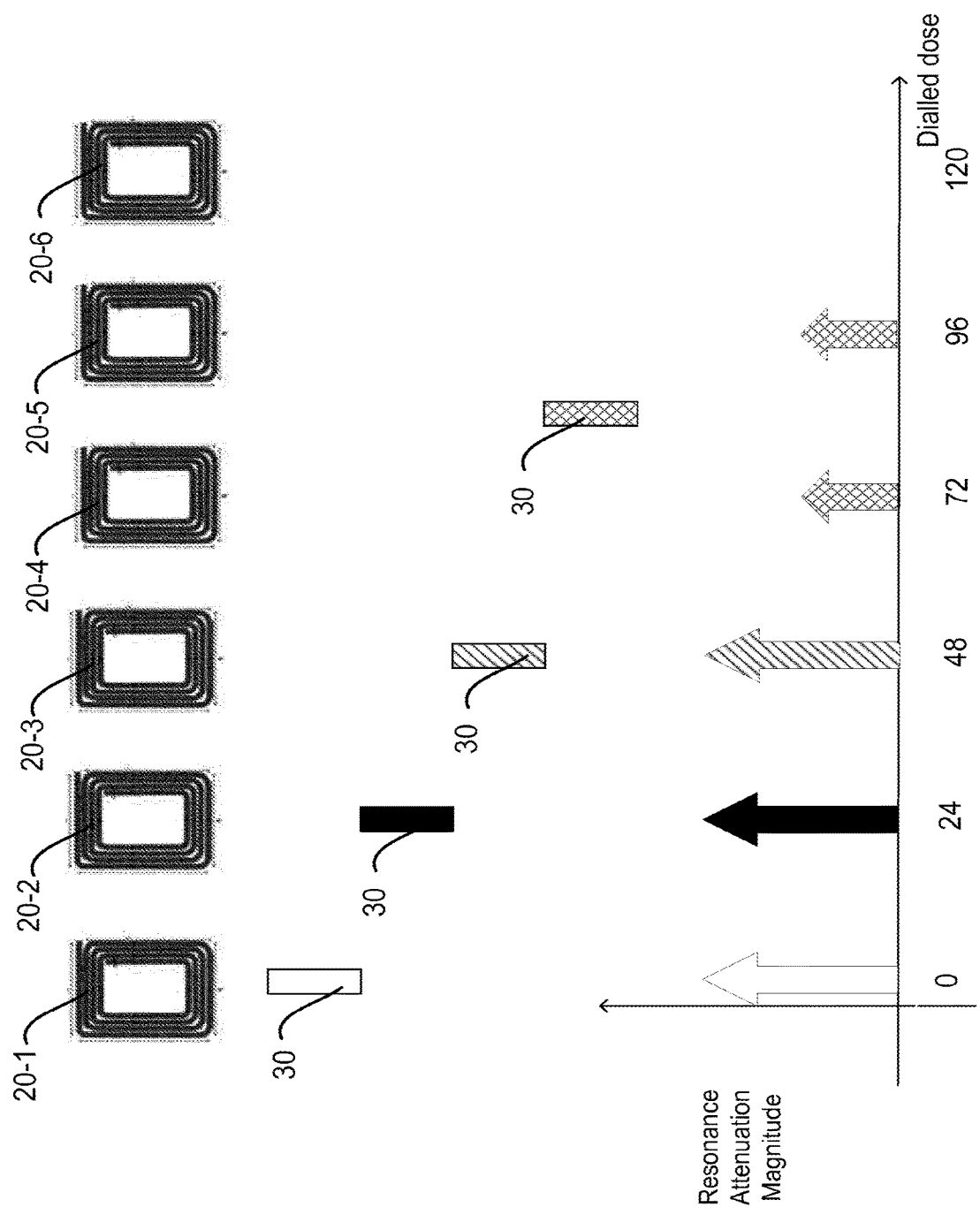
FIG. 4E illustrates the attenuation of resonance detected by the sensor device 2 and different dose are dialed into the drug delivery device.

FIG. 4E is a diagram illustrating the signals received by the processor 21 when the gauge element is in various positions along its path of movement. The conductive region 30 is illustrated in four different positions with respect to the conductive elements 20-1 to 20-6. These positions correspond to those shown in FIGS. 4A to 4D. When the conductive region 30 is located underneath the first element 20-1, the resonance magnitude detected by the processor 21 form the first element 20-1 is strongly attenuated, as illustrated by the white arrow. This position corresponds to a dialed dose of zero. The resonance detected from the other coils is not attenuated. When the conductive region 30 is located underneath the second and third elements respectively, the resonance of these elements is attenuated as illustrated by the black and hatched arrows. When the conductive region 30 is located mid-way between the fourth and fifth elements, then the resonance of both the fourth and fifth elements is attenuated, but less strongly than when the conductive region 30 is located directly underneath an element, as illustrated by the cross-hatched arrows. This position corresponds to a dose of approximately 84. This information can be used to determine that the number sleeve has undergone between 3 and 4 full rotations.

From the above, it is clear how the signals output from the conducting elements 20-1 to 20-6 can be used by the circuitry 21 to determine the approximate position of the gauge element 14. The number of completed turns of the number sleeve 15A can then be inferred from this position information.

In some alternative embodiments, the sensor device 2 may have more or fewer conductive elements, depending on the number of complete revolutions which the number sleeve may perform. In general one more conductive element than the number of rotation is provided. In the example described above, the number sleeve rotates five times to move from the zero dose position to the maximum dose position. Thus six conductive elements are provided.

As will be appreciated, the accuracy with which the dose can be determined using the array 20 of conducting elements 20-1 to 20-6 is limited by the number of elements in the array, with a higher number of elements providing a higher accuracy. An alternative mechanism for improving the accuracy of the sensor device 2 (instead of simply increasing the number of elements in the array 20) is discussed with reference to FIGS. 5A to 5C.

FIG. 5A shows an example of a rotatable element 65A, in this instance a number sleeve 65A, which may form part of a drug delivery device 6 for use with sensor devices 2 according to embodiments of the disclosure. FIG. 5B shows a simplified view of a delivery device 6 including the rotatable element 65A of FIG. 5A. The delivery device of FIG. 5B may be generally the same as that described with reference to the previous figures except for the differences described below.

As with the previously described delivery device 1, the rotation of the rotatable element 65A is interdependent with the axial movement of the movable gauge element 14. The degree of rotation may be proportional to the axial movement of the movable gauge element 14. In the examples of FIGS. 5A and B, the rotatable element 65A has, provided around its exterior surface, a visually-distinguishable code 66 for allowing its rotational orientation to be determined. For instance, the code may enable determination by the sensor device 2 as to whether the rotational orientation is zero degrees, 90 degrees, 180 degrees, 270 degrees. A rotation of zero degrees corresponds to the initial orientation of the rotatable element 65A when the dose of the delivery device 6 is dialed to its minimum. It also corresponds to the orientation after every complete rotation of the rotatable element 65A. In other examples, the code 66 may allow a higher or lower accuracy with regards the rotational orientation of the rotatable element 65A. For instance, the code 66 may allow an accuracy of the 30 or 45 degrees or may allow an accuracy of only 180 degrees. In some embodiments, the code 66 allows every one of the 24 positions comprising one full rotation to be distinguished. The code 66 may take any suitable form so long as it allows the rotational orientation of rotatable element to be determined by the sensor device 2. In this example, the code 66 is provided at an end of the number sleeve 65A.

The housing 12 of the drug delivery device 6 includes a further aperture or window 63 through which a portion of the rotatable element 65A, on which part of the code 66 is provided, is visible. The further window 63 is positioned and oriented relative to the rotatable element 65A such that a portion of the code is externally visible through the further window 63 regardless of the rotational orientation of the rotatable element 65A. The further window 63 is positioned and oriented relative to the rotatable element 65A such that, as the rotatable element rotates through a single complete rotation, a different section of the code 66 is visible at each rotational orientation. The further aperture is, in this example, provided on a different side of the device housing 12 (or, if the housing is cylindrical or otherwise rounded, around the exterior surface of the device housing 12) from the at least one window 13A, 13B through which the movable gauge element 14 is visible. In this way, the movable gauge element 14 does not obstruct the code from view.

As shown schematically in FIG. 5C, the sensor device 2 may, in addition to the array 20 of conducting elements 20-1 to 20-6, include a further sensing arrangement 23. The sensing arrangement 23 is arranged within the sensor device 2 such that, when the sensor device 2 is attached to the drug delivery device 6, the sensing arrangement 23 is operable to read encoded information 660 (which may include the code 66) that is externally visible on the drug delivery device 6. In this example, at least part of the encoded information 660 is visible through the further window 63. In some other examples, such as are discussed below, at least part of the encoded information may be provided on a portion of the exterior of the housing 12 which underlies the sensing arrangement 23.

The sensing arrangement 23 may be of any suitable type as long as it enables the encoded information 660 to be read. For instance, the sensing arrangement may be an optical sensing arrangement comprising a camera or a small array of sensing elements, a magnetic or inductive sensing arrangement or a conductance/resistance sensing arrangement.

The circuitry 21 of the sensor device 2 of FIG. 5C is configured to determine, based on the encoded information 660, information relating to operation of the drug delivery device 6. In some specific examples, the circuitry 21 is configured to determine a current dose to which the device 6 is dialed, based on the encoded information 660 and the signals output from the conducting elements of the array 20. For instance, the signals output from the array 20 may be utilized by the circuitry 21 to determine the number of complete rotations of the rotatable element 65A that have occurred and the encoded information 660 read by the sensing arrangement 23 may be utilized to determine the rotational orientation of the rotatable element 65A. Put another way, the signals output from the array 20 may be used to determine roughly the extent of axial translation of the moveable gauge element and therefore the number of complete rotations, with the encoded information 660 read by the sensing arrangement being used with the rough determination to more precisely determine the extent of translation of the movable gauge element 14 (thereby to determine the currently dialed dose).

The array 20 may comprise one more conducting element than the number of complete rotations of the rotatable element 65A that are required to move the movable gauge element 14 from its initial to final position. The elements 20-1 to 20-6 may be distributed adjacent the conductive region 30 supporting part of the movable gauge element such that after every complete rotation of the rotatable element 65A, the output of a successive element in the array 20 changes.

The encoded information 660 (specifically, code 66) read by the sensing arrangement 23 is then used by the circuitry 21 to determine the extent of any partial rotations of the rotatable element 65A. The determined extent of partial rotation of the rotatable element 65A is then combined with the determined number of complete rotations to determine the currently dialed dose of the drug delivery device 6. This determination is illustrated in Table 3 below:

For example, if the circuitry 21 determines from the sensing arrangement 23 that the rotatable element 65A is in the initial position and determines from the conducting elements 20-1 to 20-6 that no complete rotations have occurred, then it is calculated that the rotatable element 65A is in the zero dose position. However, if the circuitry 21 determines from the sensing arrangement 23 that the rotatable element 65A is in the initial position and determines from the conducting elements 20-1 to 20-6 that one complete rotation has occurred, then it is calculated that a dose of "24" has been dialed into the drug delivery device 1. Similarly, if the circuitry 21 determines from the sensing arrangement 23 that the rotatable element 65A is in the 11th position (of the 24 possible) and determines from the conducting elements 20-1 to 20-6 that four complete rotations has occurred, then it is calculated that a dose of "83" has been dialed into the drug delivery device 1.

Figure 6:
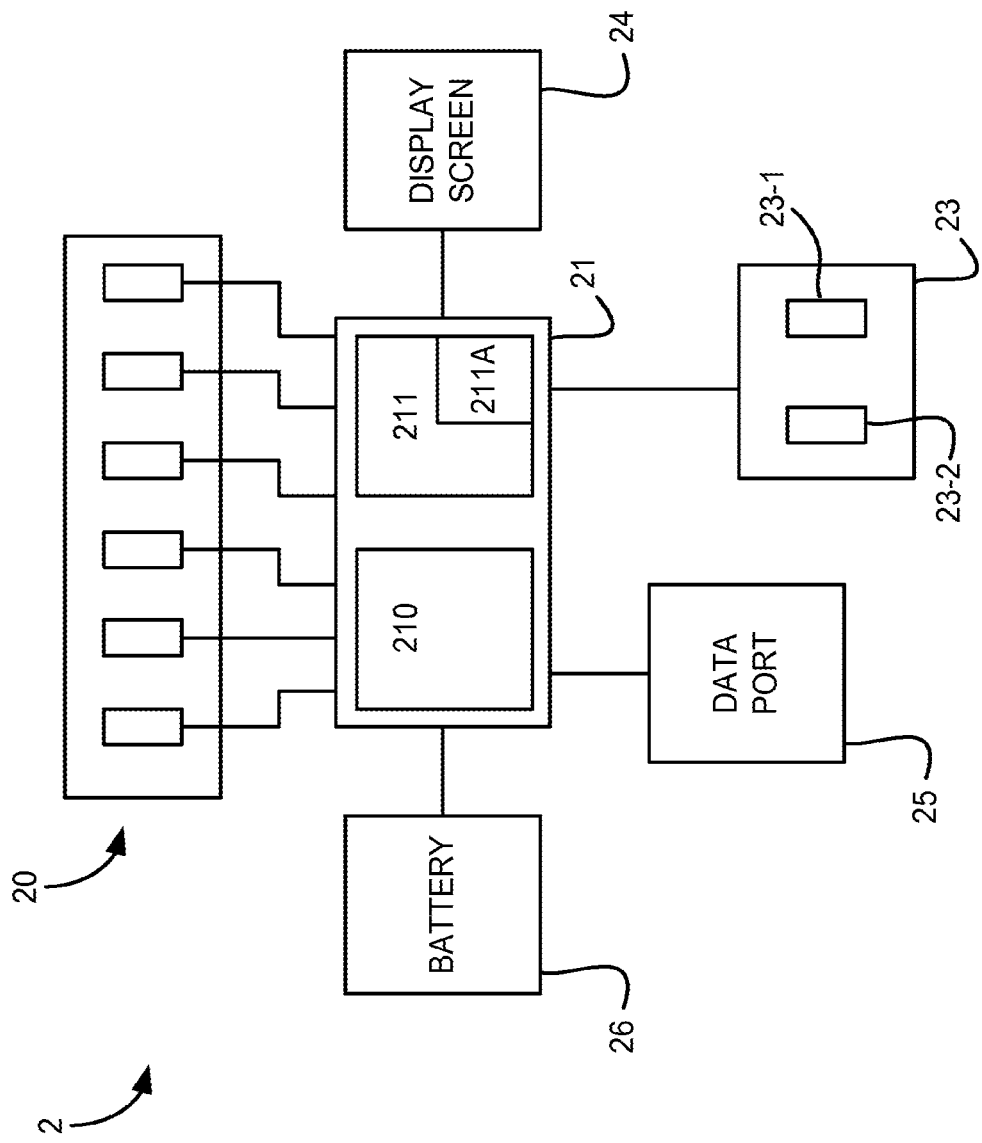
FIG. 6 is simplified block diagram of a sensor device according to embodiments of the disclosure.

Up until now, the composition of the electronic device 2 has been described at a very high level. FIG. 6 depicts the sensor device 2 in more detail.

FIG. 6 is a simplified schematic block diagram of a sensor device 2 according to various embodiments. As described above, the sensor device 2 comprises the array 20 of conducting elements 20-1 to 20-6 which are configured to output signals to the circuitry 21. In some embodiments, the device 2 comprises the further sensing arrangement 23 which is configured to output signals indicative of the encoded information to the circuitry 21.

The circuitry 21 may be of any suitable composition and may comprise any combination of one or more processors and/or microprocessors 210 (for simplicity, hereafter referred to as "the at least one processor") suitable for causing the functionality described herein to be performed. The circuitry 21 may additionally or alternatively comprise any combination of one or more hardware-only components such as ASICs, FPGAs etc. (which are not shown in FIG. 6).

The circuitry 21 may further comprise any combination of one or more non-transitory computer readable memory media 211, such as one or both of ROM and RAM, which is coupled to the at least one processor 210. The memory 211 may have computer-readable instructions 211A stored thereon. The computer readable instructions 210, when executed by the at least one processor 210 may cause the sensor device 2 to perform the functionality described in this specification, such as controlling operation of the array 20 and sensing arrangement 23 and interpreting the signals received therefrom.

The sensing arrangement 23 comprises at least a light source 23-2 and a photosensor 23-1. The light source 23-2 is for illuminating the encoded information 66 that is visible within the further window 63 formed in the device housing 62. The photosensor 23-1 is configured read the encoded information by detecting an image (which includes the encoded information 660) which is visible to the photosensor (i.e. which underlies the photosensor). The image is detected by detecting the light reflected back from different parts of the surface(s) on which the image is provided. The encoded information 660 is then passed to the circuitry 21. The sensing arrangement 23 may comprise further non-electrical components, which are not shown on FIG. 6.

Figure 7B:
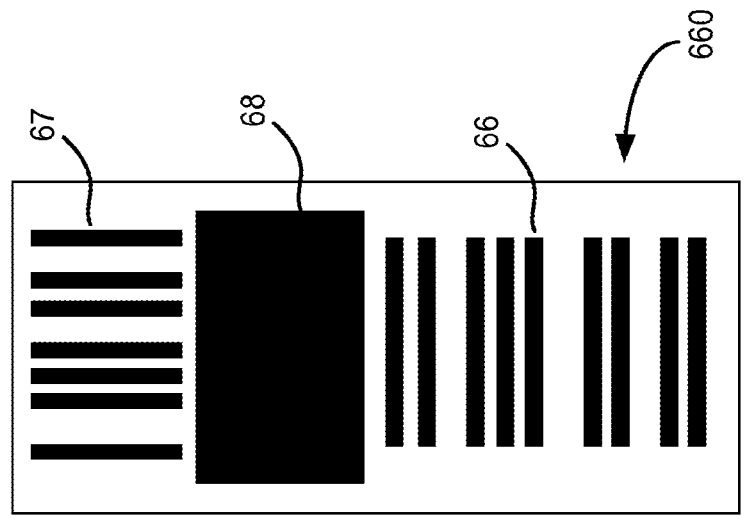
FIGS. 7A and 7B show examples of encoded information which may be read by the sensor device according to various embodiments of the disclosure.
Figure 7A:
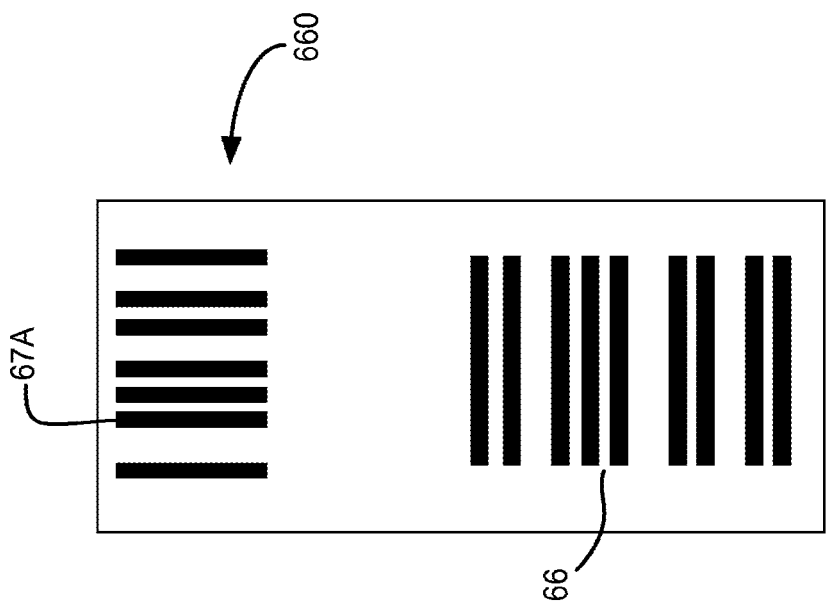

The sensor device 2 may further comprise one or both of a display screen 24 (such as an LED or LCD screen) and a data port 25. The display screen 24 may be operable under the control of the circuitry 21 to display information regarding operation of the drug delivery device 1 to the user. For instance, the information determined by the sensor device 2 may be displayed to the user. The information determined by the sensor device 2 may include the dialed dose. Other information which can be determined by the sensor device 2 includes the drug being dispensed, the mode of the drug delivery device 1, 6, and or a history of previously-dispensed doses. The determination of this "other information" is discussed below with respect to FIGS. 7A and 7B.

The data port 25 may be used to transfer stored information relating to the operation of the drug delivery device 6 from the memory 211 to a remote device such a PC, tablet computer, or smartphone. Similarly, new software/firmware may be transferred to the sensor device via the data port 25. The data port 25 may be a physical port such as a USB port or may be a virtual, or wireless, port such as an IR, WiFi or Bluetooth transceiver.

The sensor device 2 may further comprise a removable or permanent (preferably rechargeable with e.g. photovoltaic cells) battery 26 for powering the other components of the device 2. Instead of the battery 26, a photovoltaic or capacitor power source may be used. Other electrical components which are not shown in FIG. 6, but which may nonetheless be included in the sensor device 2 include a trigger buffer 27-1, a regulator 27-2, a voltage suppressor 27-3 and a charger chip 27-4, for charging the rechargeable battery if present.

As discussed above, the encoded information 660 that is read by the sensing arrangement 23 may include a portion of a code 66 for enabling the circuitry to determine the rotational orientation of the rotatable element 15A, 65A. However, in some embodiments, other operational information may alternatively or additionally be included in the encoded information 660 that is read by the sensing arrangement. For instance, the encoded information 660 may include a portion 67 (for instance in the form of a bar code) for indicating the drug that is being delivered. This can be seen in FIGS. 7A and 7B which show examples of two different views of the encoded information that may be visible to the photosensor of the sensing arrangement 23. At least part of the encoded information 660 (such as the portion of the code 66) may be visible through the further window 63 of the drug delivery device 6. The drug indication code portion 67 may be provided on, for instance, a portion of a drug cartridge that is inserted into the drug delivery device 1, 6 and which is visible through the further window 63 and so can be read by the sensing arrangement 23. Alternatively, it may be provided on a portion of the exterior of the delivery device housing 12 that is adjacent the further window 63 and which is also beneath (and so readable by) the photosensor 23-1 of the sensing arrangement 23 when the sensor device 2 attached to the drug delivery device 1, 6.

The encoded information 660 may further include a portion 68 for indicating a mode of the drug delivery device 1, 6. This can be seen in FIGS. 7A and 7B which show the encoded information 660 when the device 1, 6 is in each of a dialing mode and delivery mode. In this example, when the device is in the dialing mode, the mode indicator 68 is not part of the encoded information (as shown in FIG. 10B) and when the device in the delivery mode, the mode indicator 68 is part of the encoded information 660. Consequently, by determining whether or not the mode indicator 68 is present in the encoded information 660, the circuitry 21 can determine the mode of the device 1, 6.

Figure 8:
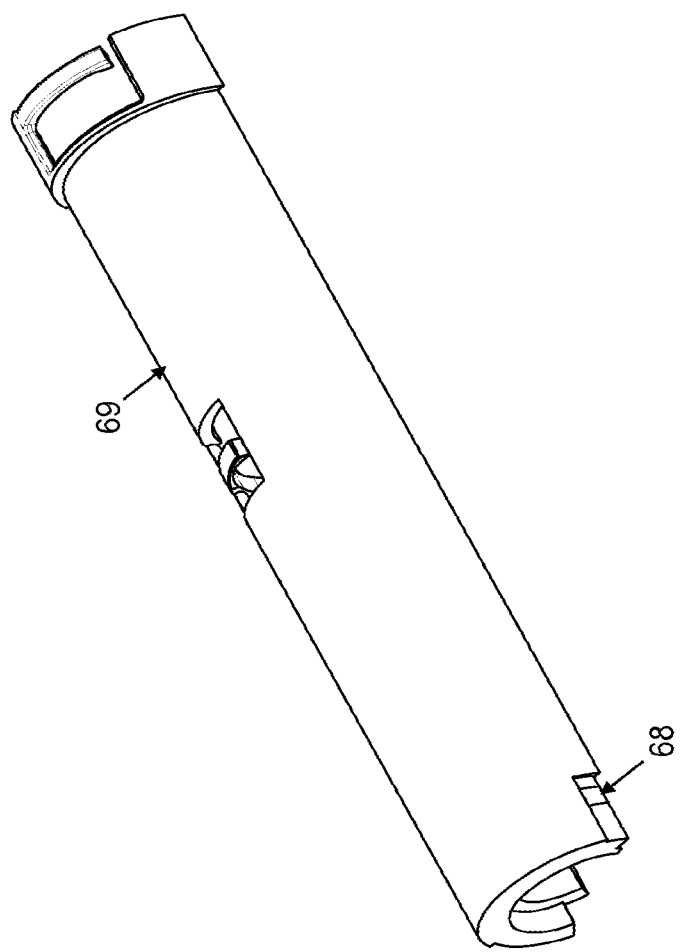
FIG. 8 shows a component of a drug delivery device for use with the sensor device according to various embodiments of the disclosure.

The mode indictor 68 may be provided on an internal element that is caused to move in response to actuation of the drug delivery mechanism (for instance by pushing the button 11). The movable internal element and drug delivery mechanism are together configured such that actuation of the drug delivery mechanism thereby to switch from dialing mode to delivery mode, causes the mode indicator 68 to become visible (or to disappear from) within the further window 63. An example of such an internal movable element 69 is shown in FIG. 8 and is a "locking arm". When situated within the drug delivery device 16, the locking arm 69 is configured to move from a first position to a second position in response to actuation of the drug delivery mechanism, e.g. by pressing on button 11. The locking arm 69 may be further configured to move from the second position back to the first position in response to subsequent actuation of the drug dialing mechanism. Alternatively, the locking arm 69 may be configured to move from the second position back to the first position in response to removing pressure from button 11. The mode indicator 68 is only visible through the window 63 when the locking arm 69 is in one of the first and second positions. In this way, the sensor device 2 is able to determine the mode of the drug delivery device 6 to which it is attached.

In some embodiments, the sensor device 2 is configured to store a history of dispensed drug doses. This may be carried out by storing information indicative of the currently dialed dose, when a change from dialing mode to delivery mode is detected based on the mode indicator 68. When the mode indicator 68 detects a change from dialing mode to delivery mode, the currently dialed dose information indicates the dose that is to be dispensed. The sensor device 2 can take this information as a dispensed drug dose. Alternatively, the sensor device 2 can calculate the dispensed drug dose from the currently dialed dose and the zero dose that is determined at the end of the dispense action. Further alternatively, the sensor device 2 can calculate the dispensed drug dose from the currently dialed dose at the time the mode indicator detects a change to dispense mode and the currently dialed dose at the time the mode detector detects a change to dial mode. A timestamp indicative of a time at which the mode change occurred may also be stored in association with the information indicative of the dose. In addition or alternatively, information indicative of the type of the dispensed drug, which is determined based on the drug indication code portion 67, may be stored in association with the dose information. This may be repeated each time a dose of a drug is dispensed.

It should be realized that the foregoing embodiments should not be construed as limiting. Other variations and modifications will be apparent to persons skilled in the art upon reading the present application. Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated. The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis. Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine. Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')₂ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immuno-pharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. A drug delivery system comprising:
a sensor device comprising:
an array of conducting elements each forming part of a respective resonant circuit and each operable to have a signal applied, wherein the array of conducting elements are arranged within the sensor device such that, when the sensor device is attached to the drug delivery device, the drug delivery device having a first movable element which is configured to move along a path parallel to a longitudinal axis of the drug delivery device and which supports thereon a conductive region, each resonant circuit is operable to output a signal indicative of the proximity of the conductive region supported on the first moveable element to the respective conducting element of each resonant circuit, and
circuitry configured to receive the signals output from each resonant circuit and, based on the received signals, to determine information associated with a location along the path of the first movable element; and
the drug delivery device having the first movable element which is configured to move along the path and a second movable element which is rotatable within the device,
wherein rotation of the second movable element and movement of the first movable element are interdependent, the second movable element comprising a code provided around a portion of an exterior of the second movable element, a part of the code being externally visible through a window or aperture formed in the drug delivery device, and
wherein the sensor device comprises a sensing arrangement overlying the window or aperture and configured to read the portion of the code that is externally visible through the window or aperture, the circuitry being configured to determine, based on the externally visible portion of the code and the position along the path of the first movable element, information relating to drug dose to which the drug delivery device is currently dialed.

2. The drug delivery system of claim 1, wherein the first movable element is moveable along an underlying element and is configured such that movement of the first movable element in a particular direction causes the underlying element to become externally visible at successive locations along the path.

3. The drug delivery system of claim 1, wherein each of the resonant circuits has a different resonance frequency.

4. The drug delivery system of claim 1, wherein the array of conducting elements is arranged within the sensor device such that, when the sensor device is attached to the drug delivery device, the conducting elements of the array are spaced equidistantly from one another along a length corresponding to the maximum extend of movement of the first moveable element.

5. The drug delivery system of claim 1, wherein the circuitry is configured to measure the amplitude of the resonant signal output from each of the resonant circuits and to determine an amount of damping of each resonant signal due to the proximity of the conductive region supported on the first moveable element.

6. The drug delivery system of claim 1, wherein the circuitry is configured to determine, based on the portion of the code that is externally visible, a degree of rotation of the second movable element within the drug delivery device.

7. The drug delivery system of claim 6, wherein the circuitry is configured to determine the information relating to drug dose to which the drug delivery device is currently dialed based on the location along the path of the first movable element and the degree of rotation of the second movable element.

8. The drug delivery system of claim 1, wherein the circuitry is configured to determine, based on the portion of the code that is externally visible, a change in an operational mode of the drug delivery device.

9. The drug delivery system of claim 8, wherein the sensor device is configured to store a history of dispensed drug doses based on at least information relating to the change in an operational mode of the drug delivery device and the information relating to a drug dose to which the drug delivery device is currently dialed.

10. The drug delivery system of claim 8, wherein the circuitry is configured to determine a change from a dialing mode to a dispense mode and/or to determine a change from a dispense mode to a dialing mode.

11. The drug delivery system of claim 8, wherein the determination of a change in the operational mode of the drug delivery device is used to further process the information relating to drug dose to which the drug delivery device is currently dialed.

12. The drug delivery system of claim 1, wherein the sensor device is further configured to transfer stored information relating to the operation of the drug delivery device to a remote device.

13. The drug delivery system of claim 1, wherein the circuitry is configured to determine a dose size to be dispensed and/or a dose size dispensed based on the information relating to drug dose to which the drug delivery device is currently dialed.

14. The drug delivery system of claim 1, wherein the sensing arrangement is arranged within the sensor device such that, when the sensor device is attached to the drug delivery device, the sensing arrangement is operable to detect light received from the aperture or window.

15. The drug delivery system of claim 14, wherein the sensing arrangement comprises:
a light source configured to project light towards the aperture or window in the drug delivery device when the sensor device is attached to the drug delivery device; and
a photosensor configured to receive light reflected from the aperture or window.

16. The drug delivery system of claim 1, wherein the drug delivery device comprises a container having a pharmaceutically active compound.

17. The drug delivery system of claim 1, wherein each conducting element in the array comprises at least one metal coil.

18. The drug delivery system of claim 17, wherein each conducting element in the array comprises one or more three dimensional metal coils.

19. The drug delivery system of claim 1, wherein the drug delivery device comprises a drug indication code arranged on an outside of the drug delivery device.

20. The drug delivery system of claim 1, wherein the sensor device comprises a sensor configured to detect the drug indication code.

* * * * *

UNITED STATES PATENT AND TRADEMARK OFFICE
CERTIFICATE OF CORRECTION

| | | |
|---|---|---|
| PATENT NO. | : 11,813,437 B2 | Page 1 of 1 |
| APPLICATION NO. | : 17/181588 | |
| DATED | : November 14, 2023 | |
| INVENTOR(S) | : Thomas Klemm et al. | |

It is certified that error appears in the above-identified patent and that said Letters Patent is hereby corrected as shown below:

In the Specification

In Column 1, Line 11 (approx.), after "filed" delete "in"

Signed and Sealed this
Thirtieth Day of January, 2024

Katherine Kelly Vidal
*Director of the United States Patent and Trademark Office*